(12) United States Patent
Galbiati (10) Patent No.: US 10,314,551 B2
(45) Date of Patent: Jun. 11, 2019

(54) DETECTOR, THREE-DIMENSIONAL DIRECT POSITRON IMAGING UNIT, AND METHOD TO ESTIMATE THE DIFFERENTIAL OF THE RADIATION DOSE PROVIDED TO CANCER CELLS AND HEALTHY TISSUES DURING HADROTHERAPY

(71) Applicant: Cristiano Galbiati, Princeton, NJ (US)

(72) Inventor: Cristiano Galbiati, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 15/184,318

(22) Filed: Jun. 16, 2016

(65) Prior Publication Data
US 2016/0367205 A1    Dec. 22, 2016

(30) Foreign Application Priority Data
Jun. 16, 2015    (IT) .................. 102015000024439

(51) Int. Cl.
*A61B 6/03*     (2006.01)
*G01T 1/20*     (2006.01)
(Continued)

(52) U.S. Cl.
CPC ............ *A61B 6/037* (2013.01); *A61B 6/0421* (2013.01); *A61N 5/1071* (2013.01); *G01T 1/023* (2013.01);
(Continued)

(58) Field of Classification Search
CPC .... A61B 6/037; A61B 6/0421; A61N 5/1071; A61N 2005/1087; A61N 2005/109;
(Continued)

(56) References Cited

U.S. PATENT DOCUMENTS

| | | | | |
|---|---|---|---|---|
| 7,439,509 B1 * | 10/2008 | Grazioso | ............... | G01T 1/2018 250/338.4 |
| 8,859,973 B2 * | 10/2014 | Moskai | ................. | G01T 1/2985 250/363.01 |

(Continued)

OTHER PUBLICATIONS

Gallin-Martel et al.,"Experimental study of a liquid Xenon PET prototype module", arXiv:physics/0211065v2 [physics.med-ph] Nov. 23, 2005.
(Continued)

*Primary Examiner* — Christine S. Kim
(74) *Attorney, Agent, or Firm* — Meagher Emanuel Laks Goldberg & Liao, LLP (57) ABSTRACT

Disclosed is a detector for a positron imaging unit, comprises a hollow body with an inner cylindrical wall and an outer wall spaced apart from the inner cylindrical wall. The hollow body includes a scintillating material, suitable to emit photons once hit by a 511 keV γ-ray, and one or more pairs of photo-detecting units (e.g. comprising PMTs or SiPM) for detecting photons emitted by the scintillating material; each photo-detecting unit of a pair being placed at opposite ends of the inner cylindrical wall along a radial direction. The scintillating material has scintillation decay time τ lower than 10 ns, an atomic number greater than 10, and a high scintillation yield greater than 8,000 photons/MeV, and comprises a mixture of xenon and argon. An imaging unit including the detector and a method to estimate the differential of the dose of radiation provided in a subject to cancer cells and to surrounding tissues in the course of hadrotherapy is also disclosed.

13 Claims, 4 Drawing Sheets

(51) Int. Cl.
  *G01T 1/24* (2006.01)
  *G01T 1/02* (2006.01)
  *A61B 6/04* (2006.01)
  *A61N 5/10* (2006.01)
  *G01T 1/204* (2006.01)
  *G01T 1/29* (2006.01)

(52) U.S. Cl.
  CPC .............. *G01T 1/026* (2013.01); *G01T 1/204* (2013.01); *G01T 1/2018* (2013.01); *G01T 1/249* (2013.01); *G01T 1/2985* (2013.01); *A61N 2005/109* (2013.01); *A61N 2005/1087* (2013.01); *A61N 2005/1094* (2013.01)

(58) Field of Classification Search
  CPC . A61N 2005/1094; G01T 1/023; G01T 1/026; G01T 1/2018; G01T 1/204; G01T 1/249; G01T 1/2985
  See application file for complete search history.

(56) References Cited

U.S. PATENT DOCUMENTS

| | | | | |
|---|---|---|---|---|
| 2002/0074505 | A1* | 6/2002 | Francke | G01T 1/185 250/389 |
| 2007/0001118 | A1* | 1/2007 | Srivastava | C09K 11/7705 250/361 R |
| 2007/0080296 | A1* | 4/2007 | Ueno | G01T 1/2985 250/363.04 |
| 2010/0099976 | A1* | 4/2010 | Tauchi | G01T 1/1642 600/411 |
| 2011/0024639 | A1* | 2/2011 | Dazeley | G01T 1/22 250/366 |
| 2012/0126127 | A1* | 5/2012 | Duraj | G01T 1/1647 250/369 |
| 2013/0032722 | A1* | 2/2013 | Szupryczynski | G01T 1/20 250/366 |
| 2015/0301201 | A1* | 10/2015 | Rothfuss | G01T 1/2985 250/252.1 |

OTHER PUBLICATIONS

Amaudruz et al., "Simultaneous reconstruction of scintillation light and ionization charge produced by 511 keV photons in liquid xenon: Potential application to PET", Nuclear Instruments and Methods in Physics Research, Section A, vol. 607, No. 3, pp. 668-676, Aug. 21, 2009.

Hademenos et al., "Development of High-Resolution Liquid-Argon and -Xenon Detectors for 1 MEV-20 GEBV Gamma Rays", Nuclear Instruments and Methods in Physics Research, Section B, vol. B40/41, No. 2, pp. 1235-1238, Apr. 2, 1989.

Jerry et al., "A Study of the Fluorescence Response of Tetraphenyl-butadiene", arXiv:1001.4214v1 [physics.ins-det] Jan. 24, 2010.

Vinke, "Time-of-Flight PET with SiMP sensors on monolithic scintillation crystals", Dissertation, Rijks Universiteit Groningen, 2011.

Humm et al. "From PET detectors to PET scanners", European Journal of Nuclear Medicine and Molecular Imaging, vol. 30, pp. 1575-1597, Oct. 2, 2003.

Studenski et al. "Proton dosimetry using positron emission tomography", World Journal of Radiology, vol. 2, No. 4, pp. 135-142, Apr. 28, 2010.

Acosta-Kane et al. "Discovery of underground argon with low level of radioactive 39Ar and possible applications to WIMP dark matter detectors", Nuclear Instruments and Methods in Physics Research A, vol. 587, pp. 46-51, Jan. 2, 2008.

Xu et al., "A study of the trace 39Ar content in argon from deep underground sources", Astroparticle Physics, vol. 66, pp. 53-60, Jan. 19, 2015.

Alexander et al. "Light yield in DarkSide-10: A prototype two-phase argon TPC for dark matter searches", Astroparticle Physics, vol. 49, pp. 44-51, Aug. 29, 2013.

Agnes et al. "First results from the DarkSide-50 dark matter experiment at Laboratori Nazionali del Gran Sasso", Physics Letter B, vol. 743, pp. 456-466, Mar. 11, 2015.

D'Souza et al., "Novel positron emission tomography radiotracers in brain tumor imaging", Indian Journal of Radiological Imaging, vol. 21, No. 3, pp. 202-208, Jul. 2011.

Wu et al., "Metabolic Labeling of Mammalian Organisms with Stable Isotopes for Quantitative Proteomic Analysis", Analytical Chemistry, vol. 76, No. 17, pp. 4951-4959, Sep. 1, 2004.

Parodi et al., "A filtering approach based on Gaussian-powerlaw convolutions for local PET verification of proton radiotherapy", Phys. Med. Biol. vol. 51, pp. 1991-2009, Mar. 30, 2006.

Zhu et al., "Proton Therapy Verification with PET Imaging", Theranostics, vol. 3, No. 10, pp. 731-740, Sep. 19, 2013.

McClatchy et al, "15N Metabolic Labeling of Mammalian Tissue with Slow Protein Turnover", Journal of Proteome Research, vol. 6, pp. 20052010, Mar. 22, 2007.

* cited by examiner

DETECTOR, THREE-DIMENSIONAL DIRECT POSITRON IMAGING UNIT, AND METHOD TO ESTIMATE THE DIFFERENTIAL OF THE RADIATION DOSE PROVIDED TO CANCER CELLS AND HEALTHY TISSUES DURING HADROTHERAPY

CROSS-REFERENCE TO RELATED APPLICATIONS

This application claims benefit of Italian Patent Application No. 102015000024439, filed Jun. 16, 2015, which is hereby incorporated in its entirety by reference.

BACKGROUND OF THE INVENTION

Positron emission tomography (PET) is a medical imaging technique that is commonly used to produce three-dimensional images of subjects' bodies inner organs and parts. This technique hinges on detection of the two 511 keV γ-rays emitted as a consequence of annihilation of an electron present in the subjects' tissues with a positron emitted by radionuclides inoculated to subjects in form of specific tracers (e.g., $^{18}F$-loaded fluorodeoxyglucose $^{18}F$-FDG). The clinical analysis of interest determines the choice for the tracers, which are selected to target specific cells or proteins based as it is made possible by their affinity for the metabolic processes. Information resulting from the determination of the position of interactions of the two 511 keV γ-rays with the detector and, possibly, of their Time-Of-Flight (TOF), is eventually processed with tomographic methods by computer analysis to produce three-dimensional images of tracer distribution and concentrations on the bodies of the subjects, which are then evaluated for clinical purposes as proxies of distribution and concentrations of cancer cells or cells of other types.

The determination of the position of positron annihilation vertices is limited by the finite range of positrons of the two 511 keV γ-rays. For $^{18}F$, the range in tissues is 5 mm, but the Full Width at Half Maximum (FWHM) and the Full Width at Tenth of Maximum (FWTM) of the three-dimensional displacement from emission to annihilation points are contained within 0.1 mm and 0.5 mm respectively [1]. Another limiting factor is the acollinearity of the two 511 keV γ-rays resulting from the non-zero momentum of the positron-electron system undergoing annihilation. The angular distribution is approximately Gaussian with a FWHM of ~0.5 degrees and limits the resolution in the axial and transaxial directions to $\Delta x = 0.5 \cdot D \cdot \tan(0.25°) = 0.0022 \cdot D$ [1], where D is the ring diameter, of 80 cm for PET and TOF-PET units, corresponding to an intrinsic limit in the transaxial resolution of a few (~2) mm [1].

Today's most sensitive commercial PET and TOF-PET (Time Of Flight Positron Emission Tomography) units for clinical studies achieve resolution for the 15 single event from positron annihilation of 4-5 mm in the axial and transaxial directions [2]. Today's commercial TOF-PET units however have a very poor resolution—a few cm—for the determination of the position of the single annihilation event in the radial direction, due to the sub-optimal performance of the TOF measurement for the 511 keV γ-rays. This sub-optimal performance of the TOF measurement, responsible for the very poor radial resolution, is ultimately due to the slow response of the inorganic scintillators used as positron detectors (e.g., LSO and LYSO with typical decay times in the range $\tau \sim 40-80$ ns). The best figures achieved by commercial TOF-PET units for the TOF spread of the single annihilation events are in the range $\Delta t \sim 500$ ps, resulting in a radial resolution $\Delta r = c \cdot \Delta t/2 \simeq 75$ mm [1].

The poor resolution in the radial direction results in limitations to the resolution, contrast, and brightness of the clinical image. As detailed above, the TOF-PET units commercially available today cannot resolve the position of individual positron annihilation with resolution close to the two fundamental scales of lengths of the PET described above. For this reason, it is necessary to reconstruct clinical images by tomography: i.e., first determining the two-dimensional projections in surfaces perpendicular to the positrons' line of flight, which have an intrinsic precision of 4-5 mm (axial and transaxial directions), and then combining and fitting the two-dimensional projections obtained for different angles such as to obtain a three-dimensional image, whose ultimate resolution is typically of 4-5 mm.

The use of a tomographic procedure for the reconstruction of three-dimensional images is, by its own, a strong disadvantage of commercially available PET and TOF-PET units. Tomography requires combination of images with statistics of $^{18}F$ decays much higher than would be otherwise required if the positron annihilation vertices were individually reconstructed with a linear resolution of the scale of the $^{18}F$ positron range. As a consequence, the typical activity of $^{18}F$ inoculated to patients is 10 mCi, responsible for a typical 12 mSv dose for each check-up procedure. While the dose is of limited statistical consequence for adult cancer patients, it is a major cause of concern in pediatric oncology, with young patients in remission potentially subjected to up to 20-30 check-up procedures in the course of their lives.

Another, additional, limitation of PET and TOF-PET units is their limited efficiency as γ-ray detectors and their limited energy resolution. The low efficiency in γ-ray detection stems from cost considerations: procurement of large surfaces of LSO and LYSO crystals is one of the driving costs, and this results in standard limitation of the thickness of crystals to no more than two interaction lengths. The limited energy resolution of 10-15% is due to the photoelectrons statistics at 511 keV energy afforded by inorganic crystals coupled with PhotoMultiplier Tubes (PMTs) or Silicon PhotoMultipliers (SiPMs). As discussed in the next paragraph, the limited γ-ray detection efficiency and the limited energy resolution both play a role in increasing the instrumental background.

A further limitation of PET and TOF-PET units is the low Signal-to-Noise Ratio (SNR). In PET jargon, events are subdivided in: 1) "T" events, defined as true coincidences of two 511 keV γ-rays originating from the same positron annihilation and fully adsorbed in the PET detector; 2) "S" events, defined as coincidences of 511 keV γ-rays originating from the same positron annihilation but releasing partial energy in a Compton scatter in the subjects' body, and with their cumulative energy only partially adsorbed in the PET detector; 3) "R" events, defined as random coincidence of two 511 keV γ-rays originating from two different positron annihilations. In PET and TOF-PET units, the SNR defined as the ratio T/(S+R) is in the range from 1:1 to 2:1. The limited energy resolution of PET and TOF-PET units inhibits the rejection of S events in the signal analysis phase. The limited γ-ray detection efficiency results in the necessity of usage of large $^{18}F$ activities, in turn resulting in very high rate of R events ($R_R$), typically much higher than the rate of T events ($R_T$) at normal condition of operation for PET and TOF-PET exams.

PET and TOF-PET units can be combined with hadrotherapy machines for use as In-Beam Positron Emission Tomography (IB-PET) [3]. With the IB-PET technique, the PET or TOF-PET units are operated in combination with the beam line delivering protons or $^{12}C$ nuclides for destruction of cancer cells. Detection of the 511 keV γ-rays produced by positron-emitting nuclides activated in subjects' the tissues directly by protons or $^{12}C$ nuclides delivered to the subjects is used for monitoring of the dose delivered to patients. The known art allows measuring the overall dose administered to subjects with a coarse spatial approximation. However, to date no method has been devised to monitor online the dose delivered to cancer cells relative to that delivered to surrounding healthy tissues.

For all of the above reasons, there is a need for improving positron imaging techniques.

BRIEF SUMMARY OF THE INVENTION

It is an object of the present invention to overcome the drawbacks of the background art.

In particular, it is an object of the present invention to improve the radial resolution of individual positron annihilation 5 events of known imaging techniques.

It is also an object of the present invention to permit reduction of the dose of tracer to be inoculated to subjects in order to obtain a clear clinical image.

A further object of the present invention is to produce brighter and higher contrast clinical images.

These and further objects of the present invention are achieved by means of a detector and an imaging unit comprising the features of the annexed claims, which form an integral part of the present description.

In one embodiment, a detector for a positron imaging device comprises a hollow body with an inner cylindrical wall and an outer wall spaced apart from the inner cylindrical wall. The hollow body includes a scintillating material, suitable to emit photons once hit by a 511 keV γ-ray, and one or more pairs of photo-detecting units (e.g., comprising PMTs or SiPMs) for detecting photons emitted by the scintillating material; each photo-detecting unit of a pair being placed at opposite ends of the inner cylindrical wall along a radial direction. The scintillating material has scintillation decay time τ lower than 10 ns, an atomic number greater than 10, and a high scintillation yield greater than 8,000 photons/MeV.

Inventors have found that by using a scintillating material with the above features, such as argon in liquid state, resolution is surprisingly increased in the radial direction. Resolution for the determination of the position of the single annihilation event in the radial direction is reduced to 4-5 mm compared to the few cm of commercial PET and TOF-PET using LSO or LYSO crystals. This means possibility to obtain clear clinical images by inoculating a reduced dose of radioactive tracer in the subject.

In one embodiment the scintillating material comprises a noble element in liquid state, and in that the detector comprises a cryostat adapted to keep the scintillating material in liquid state. Preferably the scintillating material comprises one or more of the following materials: atmospheric argon, $^{40}Ar$, argon depleted in $^{39}Ar$, argon-xenon mixtures, pure xenon. More preferably the scintillating material further comprises additional organic dopants or wavelength shifters. In one embodiment, the detector further comprises organic wavelength shifters covering the faces of the inner and outer walls being in contact with the scintillating material.

Use of these materials as scintillators in the detector provides good performances.

In one embodiment the volume inside the hollow body is divided into separate chambers by optical septa, and each photo-detecting unit is delimited by optical septa and by the inner and outer walls of the detector's hollow body; each photo-detecting unit comprises scintillation material and two photodetectors (e.g., SiPMs or PMTs) at two opposite sides. This solution allows an efficient collection of the scintillation light.

In one embodiment, the detector further comprises an anode and a cathode placed near a respective photodetector of each photo-detecting unit. This solution allows using the detector both as scintillation and ionization detector.

In a further embodiment, which provides an improved SNR, the detector further comprises a ultrapure shielding material, surrounding the outer wall of the detector, adapted to suppress signals induced in the scintillating material by environmental radioactive sources, and improves SNR of the detectors.

In one embodiment, the imaging unit further comprises means to force air, in particular air processed to reduce Radon concentration, inside the cavity where the subject is located. This solution improves SNR of the detector and therefore the overall performances of the imaging unit.

The invention also includes an imaging unit comprising a second hollow body comprising an inner circular cavity suitable to house a subject. A detector of the type above described is housed inside the second hollow body and with the inner wall concentric with the inner circular cavity. Processing means are operatively connected to the photo-detecting units 5 to process electrical signals output from the photo-detecting units and determine the position of emission of a positron in the subject. The invention also includes a method to use the positron imaging unit in combination with a hadrotherapy machine to measure online the differential of the dose administered to cancer cells and healthy tissues, also correlated with their reconstructed positions in three dimensions.

Further objects and advantages of the present invention will appear clearly from the following description of some illustrative and not limiting examples.

BRIEF DESCRIPTION OF DRAWINGS

The invention will be described hereinafter with reference to non-limitative examples, which are provided for explanatory, non-limitative purposes in the accompanying drawings. These drawings illustrate different aspects and embodiments of this invention and, where appropriate, the structures, components, materials and/or similar elements are indicated in the different figures with similar reference numbers.

DETAILED DESCRIPTION OF THE INVENTION

While the invention is susceptible to various modifications and alternative constructions, some of the illustrated embodiments are shown in the drawings and will be described below in detail.

It must be understood, however, that there is no intention to limit the invention to the specific illustrated embodiments, but, on the contrary, the invention intends to cover all the modifications, alternative constructions and equivalents that fall within the scope of the invention as defined in the claims.

The use of "such as", "etc.", "or" indicates non-exclusive alternatives without limitations, unless otherwise indicated.

The use of "includes" means "includes, but is not limited to", unless otherwise indicated.

Figure 1:
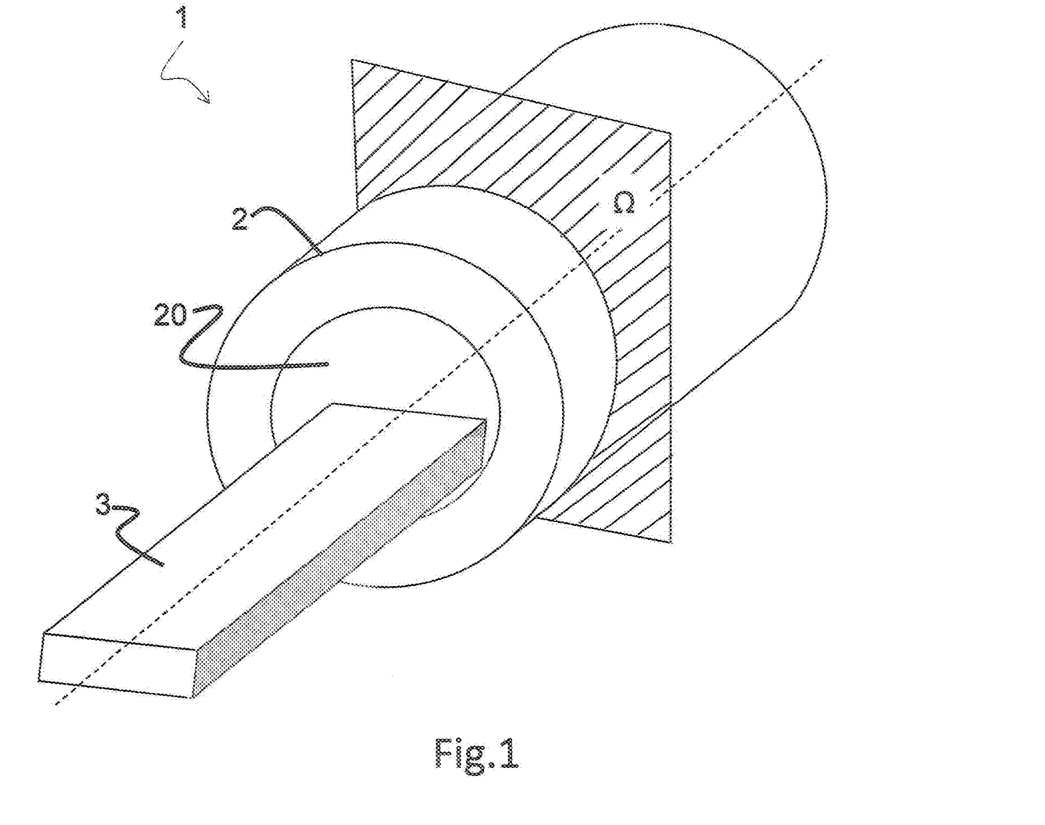
FIG. 1 illustrates an imaging unit according to the present invention.

FIG. 1 illustrates an imaging unit 1 comprising a hollow body 2 with an internal cavity 20 allowing a table 3 to slide inside out it in order to bring a subject under a detector 4 housed inside the hollow body 2.

Detector 4 is adapted to detect emission of a positron emitted in the subject lying on the table 3 and to output a electrical signals to processing means, not shown in figures, adapted to determine the position of emission of a positron in the subject.

Figure 3:
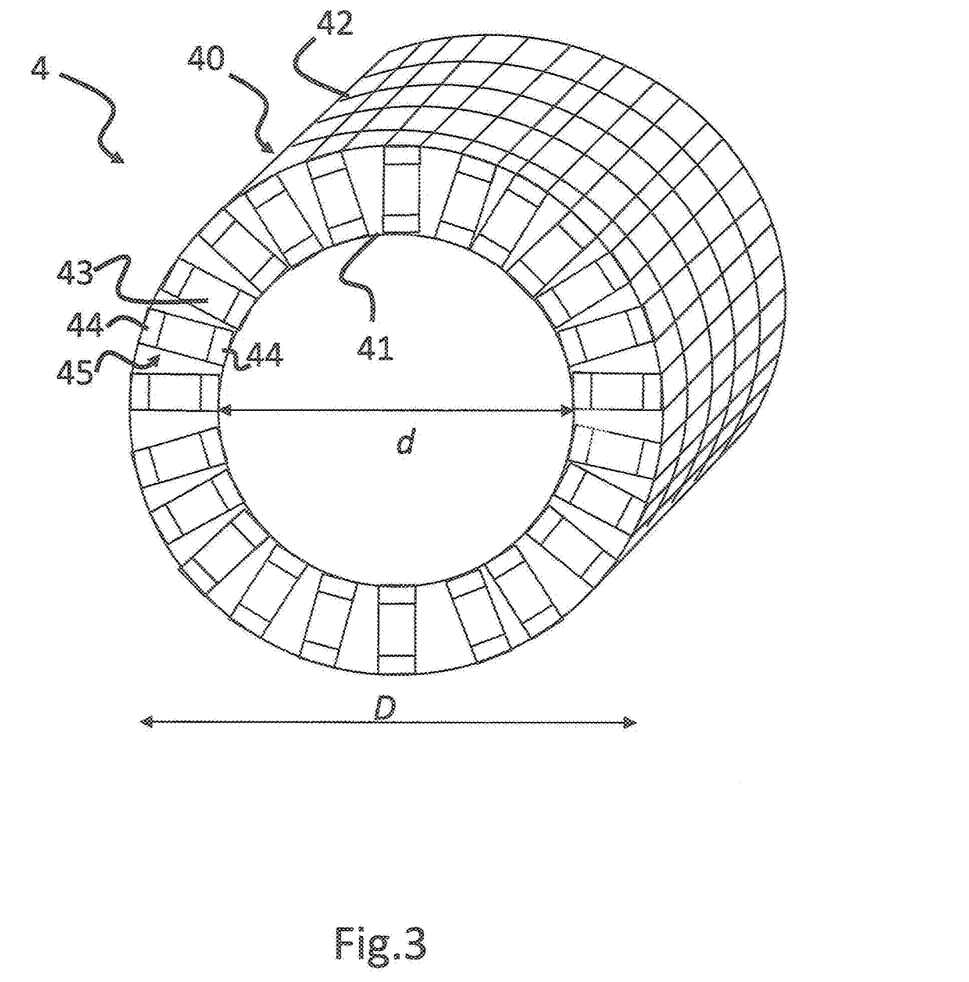
FIG. 3 illustrates a detector housed in the imaging unit of FIG. 1.

Detector 4 comprises a hollow body 40 having an inner cylindrical wall 41 and an outer wall 42. In one embodiment, the inner cylindrical wall 41 has an inner diameter d of the order of 80 cm and outer diameter D bigger than 100 cm, preferably 120 cm or larger, sufficient for an optimal containment of the 511 keV γ-rays emitted by annihilation of positrons in the tracer injected in a subject lying on the table 3. In particular, the thickness of the cylinder (distance between walls 41 and 42) is suitable to host a layer of a scintillating material (see following description) with a thickness of four interaction lengths for 511 keV γ-rays or more.

The axial length of detector 4 may cover any size from a very short (few cm) cylinder to 200 cm in case of a full-body scanner.

The hollow body 40 includes a scintillating material 43 suitable to emit photons once hit by a particle (e.g., the 511 keV γ-rays emitted during annihilation of a positron) and photodetectors (e.g., SiPM or PMTs) suitable to detect photons emitted by the scintillating material. The scintillating material is selected to have very low scintillation decay time τ, preferably lower than 10 ns, a high atomic number Z, preferably greater than 10, and a high scintillation yield, preferably greater than 8,000 photons/MeV. Requirements may be met by organic scintillators, but best performance is typically guaranteed by noble elements kept in liquid state inside a cryostat, not shown in the figures, and kept by a cryocooler at a suitable and constant temperature. The cryostat contains the full volume of the scintillating material as well as the photodetectors.

The scintillating material may be argon, and argon-xenon mixtures in any proportion, including pure xenon, with or without additional organic dopants, and/or wavelength shifters (e.g., TetraPhenylButatliene, TPB), and/or quantum splitting wavelength shifters. The addition of dopants or wavelength shifters, including the possible use of traces of xenon in argon, is preferable to convert all excited states responsible for the emission of scintillation light into fast decaying states, such as to obtain a very fast scintillator emitting photons within a few nanoseconds. In one embodiment, organic wavelength shifters are in solution in the noble element in the liquid state. In other embodiments, they could be placed on the walls of the detector facing the scintillating material.

Argon commercially available is extracted from the atmosphere and has an activity of the radioactive $^{39}$Ar of 1 Bq/kg. The tail end of β spectrum of $^{39}$Ar (Q=565 keV, $t_{1/2}$=269 yr) overlaps the Region Of Interest (ROI) for the detection of the full energy deposition peak of the 511 keV γ-rays. In one embodiment, devised for clinical studies that may require the use of a very low radioactive dose, the scintillating material comprises argon depleted in $^{39}$Ar, so as to increase the Signal-to-Noise Ratio (SNR) and, consequently the dose of radioactive tracer to be inoculated into the subject. Argon depleted in $^{39}$Ar can be obtained by use of known techniques, e.g., by extracting argon from underground sources [3,4], where the $^{39}$Ar is naturally reduced by the suppression of cosmic rays, or by active isotopic depletion, such as it may be achieved by the use of gas centrifuges or through cryogenic distillation.

In one embodiment, detector 4 is surrounded by a passive shield of ultrapure material (e.g., deionized and demineralized or distilled water with resistivity between 17 and 18 MΩ·cm, or organic liquid fluids with content of $^{238}$U and $^{232}$Th reduced below one part per trillion), surrounding all sides of the positron detector with the exception of one or two of the ends of the cylinder, suitable to suppress signals induced by environmental radioactivity to increase the SNR. The shielding material can be configured either as a passive shield or as an active anticoincidence veto detecting Cherenkov and/or scintillation photons. In one embodiment, that can be used in isolation or in combination with the passive or active shield, the detector is deployed in an underground laboratory, suppressing the background from cosmic rays and increasing the SNR.

In one embodiment, that can be used in isolation or in combination with the passive or active shield and/or the deployment in an underground laboratory, the imaging unit comprises means to force fresh air—preferably processed to reduce its Radon ($^{222}$Rn, $^{220}$Rn) concentration—inside the cavity 20 where the subjects reside. This solution further suppresses background noise and increases the SNR.

In order to detect photons emitted by the scintillating material, detector 4 comprises a plurality of pairs of photo-detecting units 45, each pair of photo-detecting units 45 being placed at opposite ends of the inner cylindrical wall 41 along a radial direction. For sake of clarity, only some radial directions are indicated by dashed lines in FIG. 2.

Figure 2:
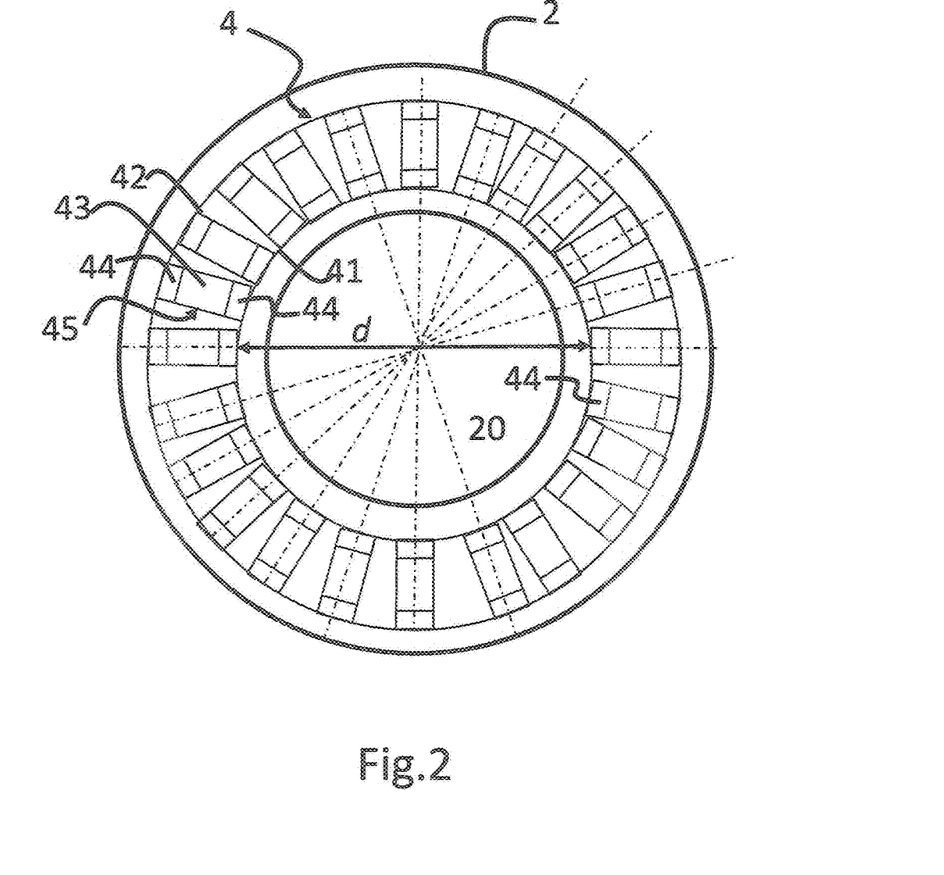
FIG. 2 illustrates a transversal section of the imaging unit of FIG. 1 along the plane Ω.

In the embodiment of FIGS. 2 and 3, the cylindrical volume of detector 3 is subdivided by optical septa in separate photo-detecting units 45 of footprint from a few $cm^2$ to a fraction of a $cm^2$. Photodetectors 44, in particular photomultipliers like SiPMs or PMTs, are placed at each radial extremity of the photo-detecting unit 45, while scintillating material 43 is comprised between the photodetectors thanks to the optical septa.

Photo-detecting units 45 output electrical signals once the photodetectors detect 511 keV γ-rays emitted by the annihilation of positrons in the subject; the output electrical signals are then processed by the processing means which determine the position of emission of a positron in the subject and reconstruct an image of the subject.

This solution allows a use of detector 4 both as scintillation-only detector or as a scintillation and ionization detector. The ionization detector could be added by providing, through a drift cage, a strong electric field capable of separating the electron-ions pairs resulting from the ionizing events in the scintillating material and drifting the electrons towards the photodetectors 44, where the electrons charge would be detected by specially devised sensors.

Some considerations are reported here below to show the performances of the above described detector.

With liquid argon doped to reduce the scintillation decay to τ~4 ns and use of high-performance SiPM at 87 K, a photoelectron yield in excess of 5,000 photoelectrons/MeV is practical and achievable [5,6]. This would result in the detection of 2,500 photoelectrons for a fully contained 511 keV γ-ray, which in turn guarantees detection of arrival of the first photons on the surface of the photo detectors in 4 ns/2,500~2 ps. Taking into account practical limitation on the time required for detection and processing in the photodetectors, a 25 resolution of Δt~30 ps is possible with the use of SiPM at cryogenic temperature or special PMTs. This would allow obtaining a position resolution in the radial direction for each T event of c Δt/2≈4 mm. At the same time, the dimensions of the voxels in the axial and transaxial directions would allow retaining the 4-5 mm resolution in those directions already achieved in commercial PET and TOF-PET units. Finally, combining the reconstructed position in three-dimensions of all events recorded, with the additional aid of advanced computer-aided algorithms, an increase in the resolution of the position of tumors to the length scale of 1 mm is expected.

Both compton- and photo-electrons can be recorded, processed and analyzed as signal. The photoelectron yield indicated above for the imaging unit would result in a 2-3% energy resolution at 511 keV, to be compared with the 10-15% of current commercial units.

Considering that:
1) Monte Carlo simulations indicate that 16% of $^{18}$F decays results in single triggers and a $3 \times 10^{-4}$ fraction of decays results in T events;
2) the typical fraction of 18F-FDG consumed by tumor metabolism is of 1%;
3) the uptake of sugar-hungry tumors such as carcinoma and breast cancer results in a 80:1 uptake relative to nearby healthy cells; and
4) detection of a tumor of size 1/10 cm$^3$ can be established, at the spatial sensitivity of 1 mm introduced above, for a conservative statistics of 1,000 localized T events. A procedure with the goal of determining size and position of a tumor of 1/10 cm$^3$ would require $3 \times 10^8$ total $^{18}$F decays, corresponding to an activity of 150 kBq or 4 μCi and to a singles trigger rate of 30 kBq.

Usage of the 10 ns coincidence window typical of traditional PET and TOF-PET units would result in a very strong suppression of the dominant background sources, R events, whose rate RR would become completely negligible. S events would be strongly suppressed by the improvement in energy resolution.

From the above description it is clear that several modification can be made by a person skilled in the art of positron imaging units and detectors for positron imaging units without departing from the scope of protection of the present invention as defined by the claims.

As an example, the cylindrical volume of detector 4 can be a single, contiguous optical volume housing the scintillation material 43 and all the photodetectors 44 instead of being divided into a plurality of volumes by optical secta like in the above described example. Photodetecting units therefore can consists of single photodetectors immersed into a scintillating material.

In one embodiment, the detectors is provided with only a pair of detectors (or voxels) placed along a radial direction at two opposite side to detect back-to-back γ-rays. In this embodiment, the positron imaging unit can be provided with means to rotate the detector 3 around the longitudinal axis.

In one embodiment, the imaging unit 1 is operated in combination with a hadrotherapy machine. The imaging unit is used as an in-beam three dimensional direct positron imaging unit, capable of determining the differential dose delivered by the hadrons beam to cancer cells relative to that delivered to surrounding healthy tissues. To this end, prior to the start of the procedure subjects are inoculated special tracers targeting cancer cells. These tracers differ from the most commonly used [$^{18}$F]FDG (Fluorodeoxyglucose, 2-Deoxy-2-[$^{18}$F]fluoroglucose, $C_6H_{11}{}^{18}FO_5$), a carrier of $^{18}$F, an unstable nuclide emitting positrons. The tracers for the in-beam three dimensional direct positron imaging are chosen among those containing nitrogen and are loaded in the stable isotope $^{15}$N (natural isotopic abundance: 0.37%) in lieu of the 20 naturally predominant $^{14}$N (natural isotopic abundance: 99.63%). For example, for a treatment of brain cancer, a suitable tracer containing nitrogen FDOPA (Fluorodopa, or 2-fluoro-5-hydroxy-L-tyrosine, $C_9H_{10}FNO_4$), whose efficiency as a tracer was demonstrated to be superior to more common [8]. FDOPA would be loaded in the $^{15}$N isotope, produced, for example, by cryogenic distillation, and, once administered to subjects in form of [$^{15}$N]FDOPA (Fluorodopa, or 2-fluoro-5-hydroxy-L-tyrosine, $C_9{}^{15}FO_4$) would preferentially concentrate in cancer cells. A possible alternative to [$^{15}$N]FDOPA is [$^{15}$N]NH$_3$. Preferably, in order to accumulate a sufficient concentration of $^{15}$N in the cancer cells of subjects, subjects will need to be inoculated sufficient quantities of tracers, possibly also in form of proteins and amino acids targeting the metabolism of cancer cells. The technique known as Stable Isotope LAbeling of Mammals tissues [9,10] results in the substitution of $^{14}$N with $^{15}$N with high percentages (>80%).

After administration of tracers loaded in the stable isotope $^{15}$N in the subject, the subjects' tissues are irradiated with a proton beam. Positron emitting nuclides are produced in the healthy tissues through reactions such as $^{16}O(p,pn)^{15}O$, $^{16}O(p,\alpha)$ $^{13}N$, $^{13}N(p,pn)^{13}N$, $^{12}C(p,pn)^{11}C$, $^{13}N(p,\alpha)^{11}C$, $^{16}O(p,\alpha pn)^{11}C$. Production of these nuclides is typically family abundant, resulting in a planar integral density of positron emitting nuclide of a few per mm for planar integral doses at the Bragg peak of a few mGy·mm$^2$ [11], which roughly translates in a positron emitting nuclide every 50-100 protons [11] and overall positron decay rates of several hundred kBq [12] at termination of a typical hadrotherapy session. In cancer cells, positron productions would be boosted by the additional channel $^{15}N(p,n)^{15}O$, which has a cross section significantly larger than $^{16}O(p,pn)^{15}O$.

In order to discriminate the dose administered to cancer cell with respect to that administered to healthy tissues, the following procedure (described with reference to FIG. 4) is applied.

Figure 4:
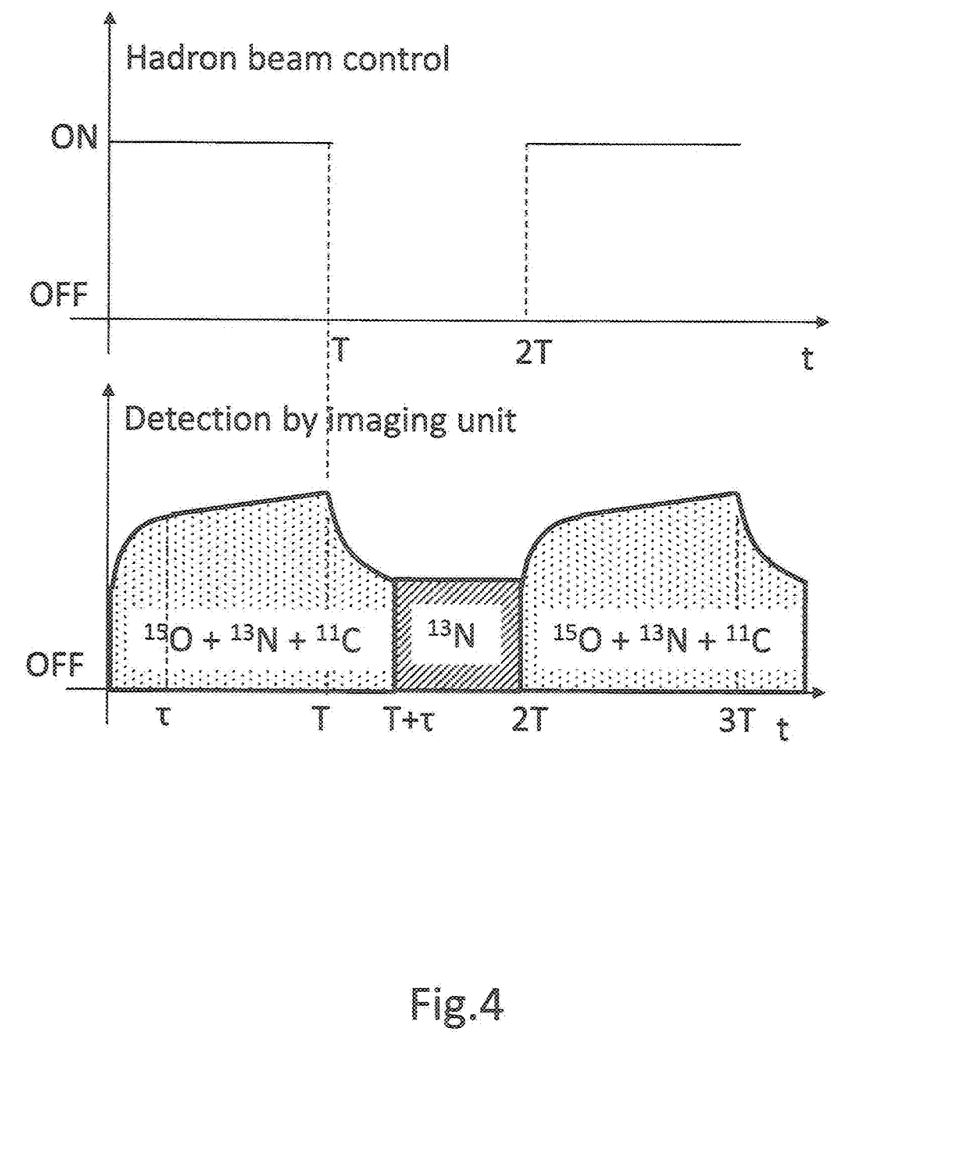
FIG. 4 illustrates diagrams relating to the control of an hadron beam and to the interpretation of images taken with an imaging unit of FIG. 1 based on control of the hadron beam.

The hadrons beam is cyclically switched on and off (see upper diagram of FIG. 4) with a period T, while the imaging unit 1 continuously takes images of subject's tissues to create three-dimensional maps of positron annihilation vertices (see lower diagram of FIG. 4).

Since $^{15}$O has a half-life of 2.0 min, much shorter than that of $^{13}$N (10.0 min) and $^{11}$C (20.4 min), the proton beam is switched on and off with a frequency comprised between 1 and 10 minutes and preferably of 4.0 minute while the positron annihilation events are continuously recorded with the imaging unit 1.

While the hadron beam is switched on and after it has been switched on for a time τ, preferably equal or bigger than the half-life of $^{15}$O, and therefore from time from τ to T with reference to FIG. 4, the imaging unit 1 takes images of positron annihilation vertices due to $^{15}$O, $^{13}$N and $^{11}$C.

While the hadron beam is switched off and after the hadron beam has been switched off for the same time T, and therefore from time T+τ to time 2T in FIG. 4, having $^{15}$O decayed much faster than $^{13}$N and $^{11}$C, the images taken after T have a strong and progressive reduction in the positron annihilation events due to $^{15}$O and therefore provide a proxy of the positron annihilation vertices due to $^{13}$N and $^{11}$C.

By subtraction of the two images, recorded in time intervals from τ to T and from T+τ to 2T, we can reconstruct the maps of the positron annihilation vertices from $^{15}$O and from $^{13}$N and $^{11}$C.

The map of the positron annihilation vertices from $^{15}$O, activated both from $^{15}$N nuclides concentrated in cancer cells and from $^{16}$O nuclides distributed in all tissues, is a proxy of the dose delivered both to cancer cells and all tissues. The map of positron annihilation vertices due to $^{13}$N and $^{11}$C, activated from $^{16}$O, $^{14}$N, and $^{12}$C, is a proxy of the dose delivered to all tissues.

From further manipulation of the two maps we can extract a proxy indicator of the differential of the dose provided to cancer cells and surrounding healthy tissues, correlated with their positions reconstructed in three dimensions.

REFERENCES

[1] R. Vinke, "Time-of-Flight PET with SiPM sensors on monolithic scintillation crystals", Disssertation, Rijks Universiteit Groningen (2011).
[2] J. L. Humm, A. Rosenfeld, A. Del Guerra, European Journal of Nuclear Medicine and Molecular Imaging 30, 1574 (2003).
[3] M. T. Studenski, Y. Xiao, World Journal of Radiology 28, 135 (2010).
[4] D. Acosta-Kane et al., Nuclear Instruments and Methods A 587, 46 (2008).
[5] J. Xu et al., Astroparticle Physics 66, 53 (2015).
[6] T. Alexander et al. (DarkSide Collaboration), Astroparticle Physics 49, 44 (2013).
[7] P. Agnes et al. (DarkSide Collaboration), Physics Letter B 743, 456 (2015).
[8] M. M. D'Souza et al., Indian Journal of Radiological Imaging 21, 202 (2011).
[9] C. C. Wu et al., Analytical Chemistry 76, 4951 (2004).
[10] D. McClatchy et al., Journal of Proteome 5 Research 6, 2005 (2007).
[11] K. Parodi and T. Bortfeld, Phys. Med. Biol. 51, 1991 (2006).
[12] X. Zhu and G. El Fakhri, Theranostics 3, 731 (2013).

What is claimed is:

1. A detector for a positron imaging unit, comprising:
a hollow body having an inner cylindrical wall and an outer wall spaced apart from the inner cylindrical wall, the hollow body including:
a scintillating material suitable to emit photons once hit by a 511 keV γ-ray;
one or more pairs of photo-detecting units for detecting photons emitted by the scintillating material, each photo-detecting unit of a pair comprising two photodetectors, and a first unit of the pair being placed at a surface of the inner cylindrical wall directly opposing a second unit of the pair;
wherein the scintillating material has a scintillation decay time τ less than 10 ns, an atomic number greater than 10, and a photoelectron yield greater than 8,000 photons/MeV; and
wherein the scintillating material comprises at least one of $^{40}$Ar, argon depleted in $^{39}$Ar, an argon-xenon mixture, or traces of xenon dissolved in argon.

2. The detector according to claim 1, wherein the scintillating material is kept in a liquid state, and the detector comprises a cryostat adapted to keep the scintillating material in the liquid state.

3. The detector according to claim 2, wherein the scintillating material further comprises at least one additional organic dopant or wavelength shifter.

4. The detector according to claim 2, further comprising at least one wavelength shifter, wherein the at least one wavelength shifter is coupled to a surface of the inner cylindrical wall and outer wall.

5. The detector of claim 1, wherein the volume inside the hollow body is divided into separate chambers by optical septa, and wherein each photo-detecting unit is delimited by at least one of the optical septa, the inner cylindrical wall, or the outer wall, and wherein each photo-detecting unit comprises scintillation material and at least one photodetector.

6. The detector according to claim 5, further comprising an anode and a cathode, each operatively connected to at least one of the two photodetectors at opposite sides, adapted to allow drift of the ionized charges and further equipped with sensing elements configured to receive an ionization signal.

7. The detector of claim 1, further comprising a shielding material located beyond the outer wall in a radial direction.

8. The detector according to claim 7, wherein the shielding material comprises at least one of deionized and demineralized water with resistivity between 17 and 18 MΩ·cm, distilled water with resistivity between 17 and 18 MΩ·cm, or organic liquid fluids with content of $^{238}$U and $^{232}$Th reduced below one part per trillion.

9. The detector according to claim 7, wherein the shielding material is configured either as a passive shield or as an active anticoincidence veto detecting Cherenkov photons, scintillation photons, or both.

10. The detector according to claim 1, wherein the concentration of xenon in the scintillating material is between and including 1 ppm and 1 ppt.

11. An imaging unit comprising:
a first hollow body comprising an inner circular cavity suitable to house a subject;
a detector housed inside the first hollow body and with an inner wall concentric with the inner circular cavity; and
a processing means operatively connected to a plurality of photo-detecting units to process electrical signals output from the photo-detecting units and determine the position of emission of a positron in the subject,
wherein the detector comprises:
a second hollow body having an inner cylindrical wall and an outer wall spaced apart from the inner cylindrical wall, the second hollow body including a scintillating material suitable to emit photons once hit by a 511 keV γ-ray;
one or more pairs of photo-detecting units for detecting photons emitted by the scintillating material, each photo-detecting unit of a pair comprising two photo detectors and a first unit of the pair being placed at a surface of the inner cylindrical wall directly opposing a second unit of the pair;
wherein the scintillating material has a scintillation decay time τ less than 10 ns, an atomic number greater than 10, and a photoelectron yield greater than 8,000 photons/MeV; and
wherein the scintillating material comprises at least one of $^{40}$Ar, argon depleted in $^{39}$Ar, an argon-xenon mixture, or traces of xenon dissolved in argon.

12. A detector for a positron imaging unit, comprising:
a hollow body having an inner cylindrical wall and an outer wall spaced apart from the inner cylindrical wall, the hollow body including:
  a scintillating material suitable to emit photons once hit by a 511 keV γ-ray;
  one or more pairs of photo-detecting units for detecting photons emitted by the scintillating material, where at least one photo-detecting unit of a pair comprises two photodetectors, and a first unit of the pair being placed at a surface of the inner cylindrical wall directly opposing a second unit of the pair;
wherein the scintillating material has a scintillation decay time τ less than 10 ns, an atomic number greater than 10, and a photoelectron yield greater than 8,000 photons/MeV; and
wherein the scintillating material comprises at least one of $^{40}$Ar, argon depleted in $^{39}$Ar, an argon-xenon mixture, or traces of xenon dissolved in argon.

13. An imaging unit comprising:
a first hollow body comprising an inner circular cavity suitable to house a subject;
a detector housed inside the first hollow body and with an inner wall concentric with the inner circular cavity; and
a processing means operatively connected to a plurality of photo-detecting units to process electrical signals output from the photo-detecting units and determine the position of emission of a positron in the subject,
wherein the detector comprises:
  a second hollow body having an inner cylindrical wall and an outer wall spaced apart from the inner cylindrical wall, the second hollow body including a scintillating material suitable to emit photons once hit by a 511 keV γ-ray;
  one or more pairs of photo-detecting units for detecting photons emitted by the scintillating material, where at least one photo-detecting unit of a pair comprises two photodetectors, and a first unit of the pair being placed at a surface of the inner cylindrical wall directly opposing a second unit of the pair;
  wherein the scintillating material has a scintillation decay time τ less than 10 ns, an atomic number greater than 10, and a photoelectron yield greater than 8,000 photons/MeV; and
wherein the scintillating material comprises at least one of $^{40}$Ar, argon depleted in $^{39}$Ar, an argon-xenon mixture, or traces of xenon dissolved in argon.

* * * * *